United States Patent
DiMatteo et al.

(10) Patent No.: US 7,201,745 B2
(45) Date of Patent: Apr. 10, 2007

(54) ANTI-INFECTIVE CENTRAL VENOUS CATHETER WITH DIFFUSION BARRIER LAYER

(75) Inventors: Kristian DiMatteo, Waltham, MA (US); Sharon Mi Lyn Tan, Brighton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/437,713

(22) Filed: May 13, 2003

(65) Prior Publication Data

US 2004/0230177 A1 Nov. 18, 2004

(51) Int. Cl.
*A61M 25/00* (2006.01)
(52) U.S. Cl. ..................................... 604/523
(58) Field of Classification Search ............... 604/264, 604/265, 266, 280, 523, 891.1; 623/12; 424/422; 514/822; 523/112; 427/2
See application file for complete search history.

(56) References Cited

U.S. PATENT DOCUMENTS

| | | | |
|---|---|---|---|
| 4,994,047 A * | 2/1991 | Walker et al. | 604/264 |
| 5,286,254 A | 2/1994 | Shapland et al. | |
| 5,520,664 A | 5/1996 | Bricault, Jr. et al. | |
| 5,562,652 A | 10/1996 | Davis | |
| 5,725,513 A | 3/1998 | Ju et al. | |
| 5,752,941 A | 5/1998 | Romano' et al. | |
| 5,810,786 A * | 9/1998 | Jackson et al. | 604/265 |
| 6,071,308 A | 6/2000 | Ballou et al. | |
| 6,599,275 B1 * | 7/2003 | Fischer, Jr. | 604/265 |
| 2003/0045861 A1 | 3/2003 | Peterson | |

FOREIGN PATENT DOCUMENTS

| | | |
|---|---|---|
| EP | 0 341 049 | 11/1989 |
| WO | WO 97/46268 | 12/1997 |
| WO | WO 99/03425 | 1/1999 |
| WO | WO 02/36194 | 5/2002 |

\* cited by examiner

*Primary Examiner*—Manuel Mendez
(74) *Attorney, Agent, or Firm*—Fay Kaplun & Marcin, LLP

(57) ABSTRACT

A catheter extending from a distal end which, when in an operative position is inserted within a body of a patient, to a proximal end, the catheter comprising a charge holding cavity to which a therapeutic compound is to be supplied and a wall including inner and outer portions, an inner surface of the inner portion surrounding the charge holding cavity with an outer portion surrounding at least a portion of an outer surface of the inner portion, wherein the inner portion is formed so that a first diffusion rate of the therapeutic compound therethrough is different from a second diffusion rate through the outer portion.

21 Claims, 4 Drawing Sheets

ANTI-INFECTIVE CENTRAL VENOUS CATHETER WITH DIFFUSION BARRIER LAYER

BACKGROUND INFORMATION

Many medical procedures require repeated and prolonged access to a patient's vascular system. For example, during treatment of diabetic patients, blood is removed for filtering and purification externally to the body, to make up for the inability of the patient's kidneys to carry out that function naturally. In other procedures, access to the patient's vascular system is necessary to administer antibiotics, drugs, nutrition or chemotherapy agents on a long term basis. Typically access is obtained through a vein or artery, using a catheter secured to the patient and a needle of the catheter penetrating the blood vessel.

Some of these procedures are repeated several times a week and it is impractical and dangerous to insert and remove the catheter for each procedure. The catheter thus is implanted semi permanently with a distal end remaining within the patient, in contact with the vascular system, and a proximal end remaining external to the patient's body. The proximal end is sealed after the medical session is completed, to prevent blood loss and infections. The distal end of the catheter thus remains in the patient's body, often for extended periods of time. In some cases, the catheter may be sutured in place and remain within the patient for several years.

A clinical drawback to leaving these devices in the patient for extended periods is that bacteria tends to attach to the surfaces of the catheter, multiply, and produce a biofilm layer that can result in sepsis. These infections may lead to severe complications that often are debilitating and may be life-threatening. Anti-infective agents including, for example, antibiotic and other antimicrobial coatings, have been used on the catheters to combat these infections. For example, chlorhexidine-silver sulfadiazine and rifampin-myinocycline coatings, among others, have been applied to the polymeric surfaces of catheters. This solution however has not proved satisfactory, as the agents in the coatings are often released in a short time interval after implantation of the device, soon leaving the catheter open to infection.

SUMMARY OF THE INVENTION

The present invention is directed to a catheter extending from a distal end which, when in an operative position, is inserted within a body of a patient to a proximal end, the catheter comprising a charge holding cavity to which a therapeutic compound is to be supplied and a wall including inner and outer portions, an inner surface of the inner portion surrounding the charge holding cavity with an outer portion surrounding at least a portion of an outer surface of the inner portion, wherein the inner portion is formed so that a first diffusion rate of the therapeutic compound therethrough is different from a second diffusion rate through the outer portion.

DETAILED DESCRIPTION

The treatment of many medical conditions requires repeated access to a patient's venous system for therapeutic sessions, for example, to carry out transfusions, administer antibiotics, drugs, nutrition or chemotherapy agents to the blood stream, or to purify a patient's blood. Kidney dialysis is one of such treatments which requires chronic access to patients' blood streams in order to treat chronic renal failure. In the case of ailments for which no cure has yet been found, these therapeutic sessions may need to be repeated periodically for the life of the patient. In many cases the sessions are required several times per week with each session lasting several hours. Cumulative damage to the skin and vascular walls caused by repeated punctures makes it impractical to introduce a new catheter into the patient's venous system at every session. Accordingly, as described above a semi-permanently implanted catheter is often used, which is maintained in place in the patient for an extended period of time. The semi-permanently implanted catheter may then be used whenever access to the venous system is required.

These implantable, semi-permanent vascular access catheters are inserted into and remain partially within the patient for extended periods. Examples of such implantable catheters include the chronic dialysis catheters and implantable vascular access systems manufactured by Boston Scientific Corp. under the trade name Vaxcel™. These devices typically are inserted through the patient's skin so that a distal end remains under the skin, within the patient's body while a proximal end extends outside the body for connection to an external line. These semi-permanent catheters may be sutured to the patient's skin to maintain them in place while the patient goes about his or her normal occupations.

Figure 1:
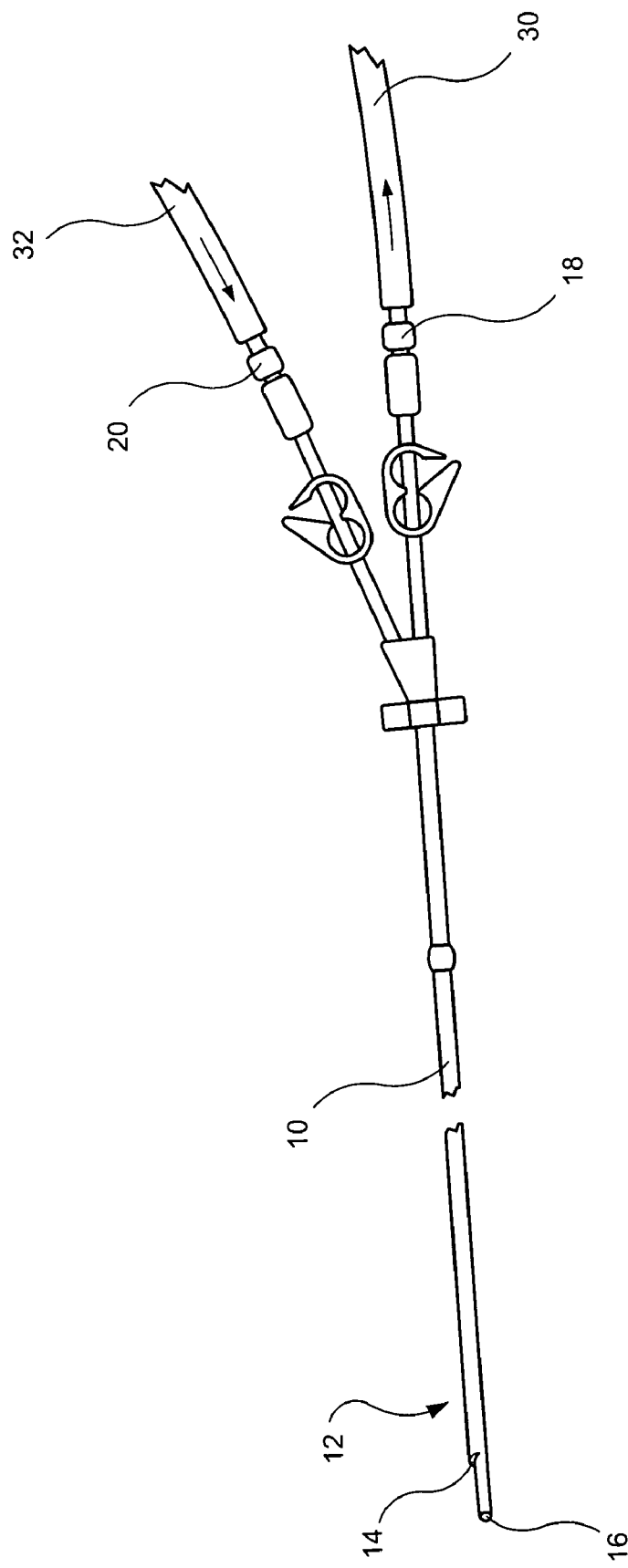
FIG. 1 is a schematic diagram of a vascular access catheter.
Figure 2:
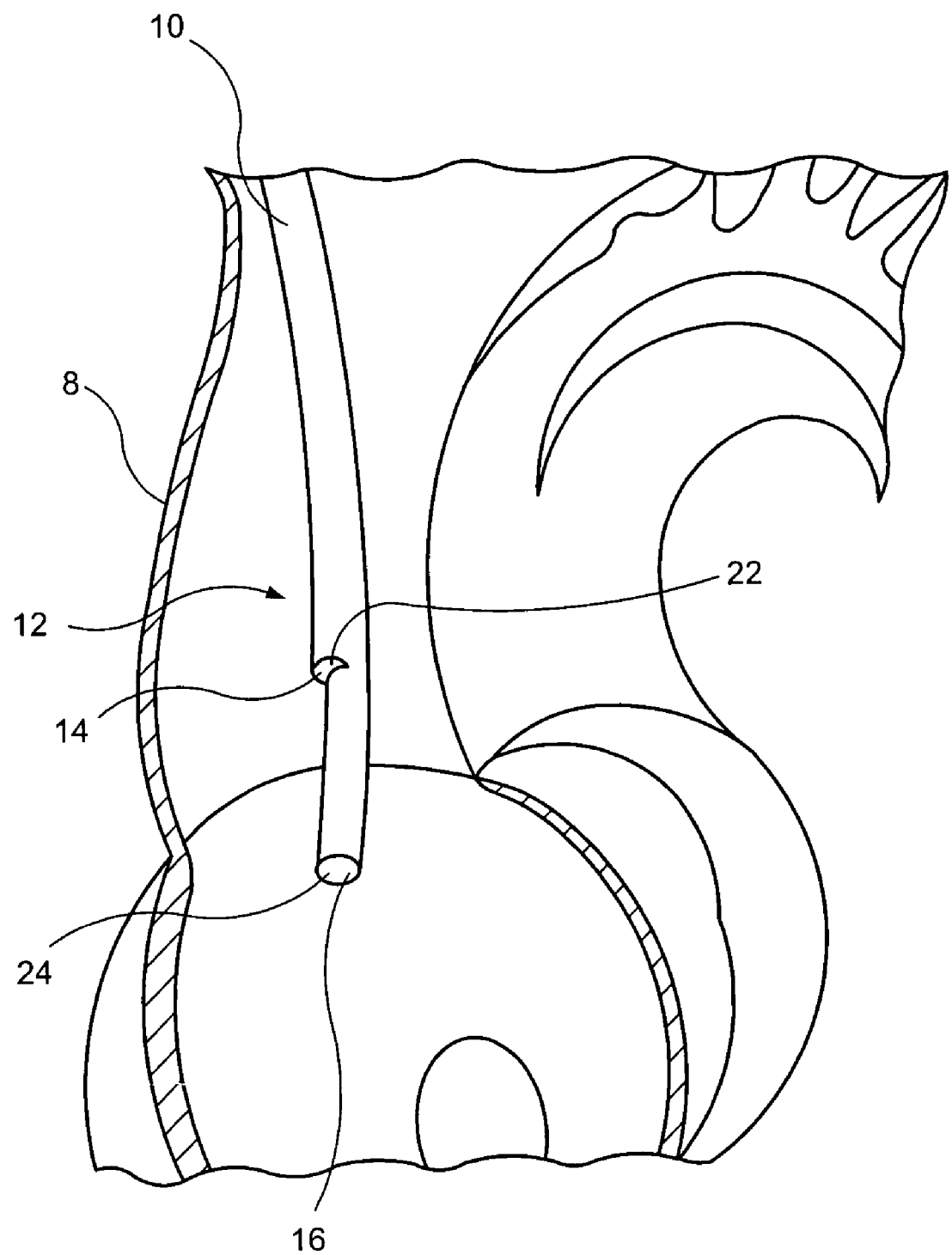
FIG. 2 is a schematic drawing of a vascular access catheter inserted in a patient's vein.

FIGS. 1 and 2 show an exemplary implantable catheter such as the Vaxcel™ Chronic Dialysis Catheter used for kidney dialysis. The catheter 10 has a distal end 12 that is insertable under the skin and into the patient's vein, and which remains within the patient's body for the life of the catheter 10. For example, the catheter 10 may remain implanted in the patient for up to two years or more. As shown more clearly in FIG. 2, the distal end 12 is inserted into a vein 8, for example the vena cava. During dialysis, blood from the patient is removed through the catheter 10, and is purified by a dialysis machine (not shown) which is connected to hubs 18 and 20 of catheter 10 by a dialysis line. The catheter 10 in this example includes a first lumen 22 which is used to remove blood from the blood vessel 8 and supply it to the dialysis machine and a second lumen 24 which receives treated blood from the dialysis machine and reintroduces it into the blood vessel 8. The lumen 22 terminates at the distal end 12 in an inflow tip 14 while the lumen 24 terminates at the distal end 12 in an outflow tip 16. The inflow and outflow tips 14, 16, respectively, may be staggered (i.e., separated from one another along the length of the distal end 12) to improve a flow of blood through the catheter 10. The first lumen 22 is connected to an inflow hub 18 while the second lumen 24 is connected to an outflow hub 20. The inflow and outflow hubs 18, 20, respectively are connected to a proximal part of the catheter 10 which, when the distal end 12 is in position within the blood vessel 8, remains outside the body for connection to a dialysis line leading to the dialysis machine. That is, the inflow hub 18 may be coupled to a first lumen of a dialysis line for supplying blood to the dialysis machine while the outflow hub 20 is coupled to a second lumen of the dialysis line for receiving treated blood from the dialysis machine and returning it to the blood vessel 8.

When implanted in the patient's body, infective growth may occur at any point along the portion of the catheter 10 which is within the patient's body. As indicated above, various coatings containing anti-infective agents have been placed on the surfaces of catheter 10 to prevent the growth of infective agents. In addition, anti-infective agents have been supplied in the form of, for example, cuffs including the anti-infective agents or a liquid supplied to a lumen of the catheter which allows anti-infective agents to leach through the catheter surface to prevent infective growth on or adjacent to the outer surface thereof. However, these methods have often resulted in a too rapid release of the agents which, after a relatively short time, leaves the catheter 10 exposed to infective growth once again.

The catheter 10 according to the invention is capable of delivering anti-infective agents both intra-luminally and extra-luminally to prevent attachment of bacteria or other infective agents to both the inner and outer surfaces of the catheter 10. According to embodiments of the invention, anti-infective agents are delivered to either or both of the first and second lumens 22, 24, respectively, of the catheter 10, for example, after completion of a therapeutic session such as a dialysis session or chemotherapy session. From the lumen to which the agent is supplied, the compounds can enter the polymeric wall of the catheter 10 and eventually reach an outer surface thereof where they may impede bacterial or other infective growth. The anti-infective agent may be provided within the lumen either in the form of a rod impregnated with the agent, as a liquid solution, or in any other manner as would be understood by those of skill in the art. For example, iodine impregnated rods may be inserted into the lumens 22, 24 or a two part solution of an iodine generating formulation may be placed in the lumens 22, 24 after the therapeutic procedure has been completed. As discussed above, after the therapeutic treatment has been completed, the proximal ends of the lumens 22, 24 are capped off to prevent infective agents from being introduced into the body via the lumens 22, 24. Thus, once the anti-infective agents have been introduced into the lumens 22, 24, the capping of the proximal ends of the lumens will maintain the liquid within the lumens 22, 24 and this liquid will not enter the blood stream. Then, to access the catheter 10 for subsequent treatments, treatment personnel need only remove the cap to access the lumens 22, 24.

This system of providing an internally stored quantity of anti-infective agents within the catheter 10 may be further supplemented by controlling a rate at which the agents pass through the wall of the catheter 10 to the outer surface thereof. This reduces the need for additional visits to health care providers to recharge the supply of anti-infective agents and the costs and inconvenience associated with such additional visits. The diffusion rate of the anti-infective agents is preferably selected so that the anti-infective action continues throughout the entire time interval between scheduled therapeutic sessions and may include a tolerance for occasions when a scheduled visit is delayed or missed.

Figure 3:
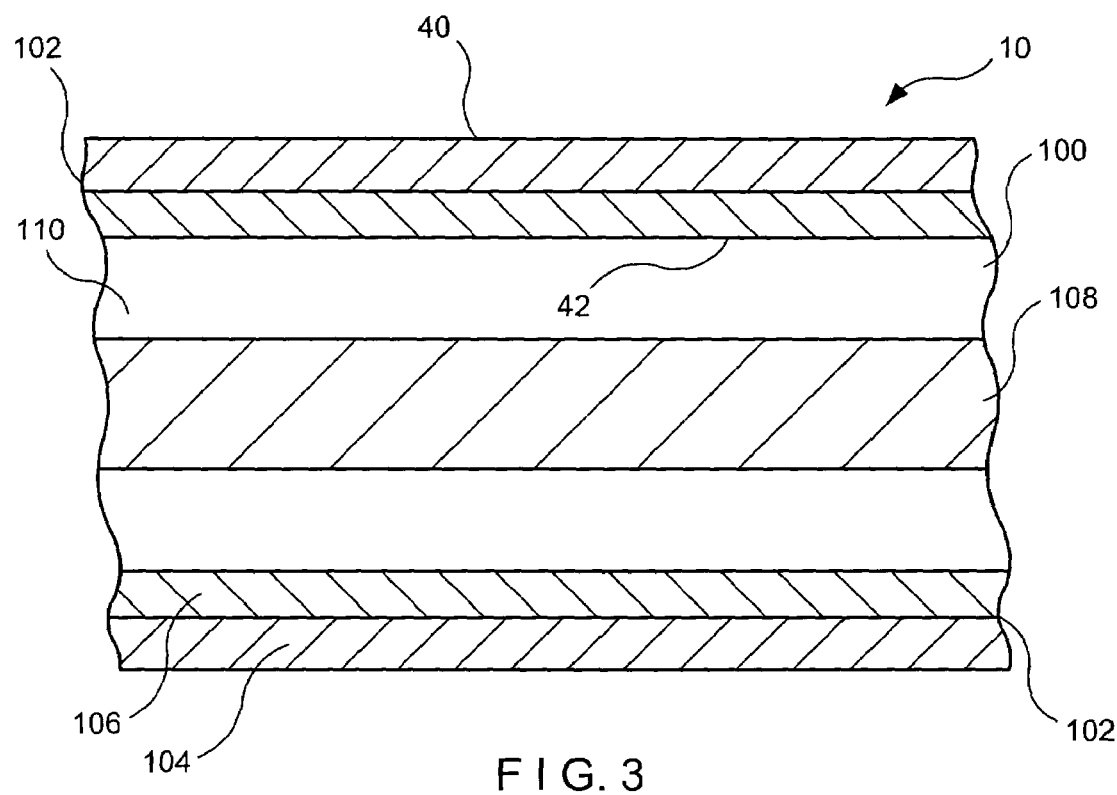
FIG. 3 is a diagram of a catheter cross section according to an embodiment of the present invention.

FIG. 3 shows an exemplary cross sectional diagram of a catheter with an anti-infective delivery system according to an embodiment of the present invention. In the exemplary embodiment, a dialysis catheter 10 is used as a venous catheter that is semi-permanently implanted in a patient. The catheter 10 is formed of a catheter body 40 which includes an outer wall 102 forming an enclosure around a lumen 100. As will be apparent to those skilled in the art, the catheter 10 may include any number of additional lumens, and is preferably formed of a flexible material which allows the catheter body 40 to bend, twist, and be deformed to a certain extent. In its simplest form, the catheter 10 is a hollow tube which includes a single lumen 100 used during therapeutic sessions to carry fluids to and from the patient's vascular system.

In the embodiment described below, one end of the catheter 10 enters a patient's vein, and the other end is connected to a device used to receive, supply and/or process medical fluids, such as blood as would be understood by those skilled in the art. The outer wall 102 of the catheter 10 forms a shell-like enclosure around the lumen 100 and has an inner surface 42 which defines the lumen 100 and will be in contact with materials 110 placed within the lumen 100. An outer surface 40 of the outer wall 102 is exposed to environment surrounding the catheter 10. For example, the surface 40 may be in contact with the contents of a body lumen into which the catheter 10 has been inserted. In the exemplary case where the catheter 10 is a dialysis catheter implanted in a patient, a proximal portion of the outer surface 40 would be in contact with the tissue through which the catheter 10 was inserted, while a distal portion of the outer surface 40 of the catheter 10 will be in contact with the blood and/or wall of one or more blood vessels. The lumen 100 may be used to transfer blood between the patient and a dialysis machine during treatment, and between treatments may be filled with an anti-infective or therapeutic compound 110 and sealed at a proximal end thereof. Those skilled in the art will understand that, in addition to anti-infective agents, the therapeutic compound may be any agent which it is desired to apply to an outer surface of the catheter 10 and, consequently, to be supplied to the surrounding environment at a controlled rate (e.g., anti-thrombotic, medicinal, nutritional or other substances).

In one embodiment, the therapeutic compound 110 may be an anti-infective agent such as a two part solution of an iodine generating solution. In a different embodiment, a rod 108 impregnated with an anti-infective agent such as iodine may be inserted in the lumen 100. In this manner, the anti-infective agent can diffuse from the rod 108 over time, between sessions. When it is necessary to carry out another therapeutic session, material is removed from the lumen 100 by aspiration or by other means so that the catheter 10 can be used for its principal function.

According to exemplary embodiments of the present invention, a rate of diffusion of the anti-infective agent from within the catheter 10 to the outer surface thereof is controlled to a first pre-selected rate. In addition, the rate at which the anti-infective agent is absorbed from the lumen 100 into an inner wall of the catheter 10 may also be selected to a second preselected rate so that, for example, the anti-infective agent is quickly absorbed into the catheter 10. In particular, the first rate may be selected so that only a necessary amount of anti-infective agent or other therapeutic compound reaches the outer surface of the catheter 10 at any given time, and so that the charge of therapeutic compound within the lumen(s) 40 of the catheter 10 lasts for a predetermined time interval. In one embodiment, a diffusion barrier layer is formed at an outer portion 104 of the outer wall 102 of the catheter, to reduce the diffusion rate therefrom. With reference to FIG. 3, the outer wall 102 of the catheter 10 is designed to allow diffusion of the therapeutic compound 110 therefrom at a controlled rate. For example, the outer wall 102 may include an inner portion 106 that has properties different than those of the outer portion 104. In this embodiment, the durometer hardness of the inner portion 106 is selected to be different than that of the outer portion 104 durometer hardness of a material is one factor which determines the rate at which iodine is absorbed thereinto. Other factors which may effect this rate are, for example, the addition of additives of different materials to the resin as described below and the treatment of the surface of the material by roughening it or creating openings therein. However, all other factors being equal, an element formed with a higher durometer hardness will generally absorb iodine less quickly than a similar element of a lower durometer hardness. Thus by using a resin with a higher hardness to form the outer portion 104, the amount of iodine passing through the outer surface 40 in a given time is less than it would have been if the outer portion 104 were made of the same lower hardness material of which the inner portion 106 is formed. This also allows the iodine to be more rapidly absorbed into the inner portion 106. This allows for treatments wherein a first injection of iodine is made into the lumen 100 which iodine is quickly absorbed into the inner portion 106. Then, after a brief waiting period during which the iodine is absorbed into the inner portion 106, the remainder of the substantially material in the lumen 100 may be removed and further desired therapeutic agents may then be supplied to the lumen 100.

In the embodiment shown in FIG. 3, the lower durometer inner portion 106 and the higher durometer outer portion 104 may preferably formed through co-extrusion of two (2) layers of different materials at the same time. This method gives rise to a uniform outer wall 102, which provides the desired differential between the rate of absorption through the inner surface 42 into the inner portion 106 and the rate of diffusion from the outer portion 104 through the outer surface 40.

Alternatively, different diffusion rates of therapeutic compounds through the inner and outer portions 106, 104 may be achieved by replacing or supplementing the polyurethane in the resin forming wall 102 with other compounds having different absorption properties. For example as would be understood by those skilled in the art, barium sulfate, titanium oxide or bismuth sub-carbonate may be added to polymer resins (e.g., polyurethane) to alter the diffusion rates of various compounds therethrough. The inclusion of these materials into the polymers reduces the inter-molecular spaces through which the diffusion takes place, thereby providing a greater barrier to the diffusion of iodine and other compounds therethrough. Thus, any of these materials, or a combination thereof, may be added to the material of the outer portion 106 to reduce the rate at which an anti-infective agent supplied to the lumen 40 reaches the outer surface 40 while, forming the inner portion 106 without the addition of such materials allows anti-infective agents to be absorbed thereinto from the lumen 40 at an increased rate. In addition, as would be understood by those of skill in the art, by selecting resins of varying molecular weights, different rates of absorption thereinto may also be obtained.

As described above, forming the outer wall 102 in a co-extrusion process may simplify the construction of the catheter 10 while allowing the properties of the outer wall 102 of the catheter 10 to be tailored to desired diffusion rates of anti-infective agents through the inner and outer portions 106, 104, respectively of the outer wall 102.

Figure 4:
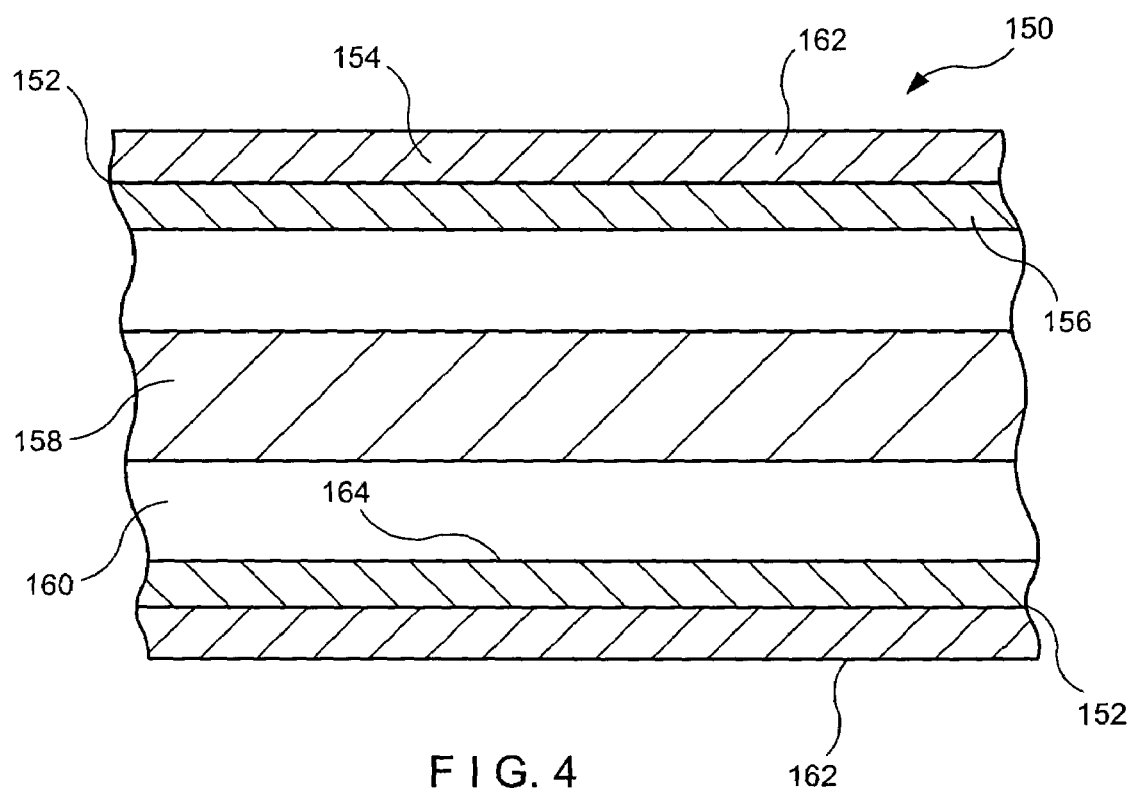
FIG. 4 is a diagram of a catheter cross section with dual material walls according to another embodiment of the present invention.

A further embodiment of the present invention is depicted in FIG. 4. Here, a catheter 150 includes an outer wall 152 that envelops a lumen 160. As described above, a therapeutic compound may be supplied to the lumen 160 in liquid form, as a rod 158 impregnated with a releasable agent, or in any other suitable form. The outer wall 152 in this exemplary embodiment is formed of two different materials, having different diffusion properties. For example, the diffusion properties of an ethylene vinyl acetate (EVA) catheter may be modified by using an outer shell of polyurethane material outside of the EVA shell.

As shown in FIG. 4, the outer wall 152 is a composite wall with an inner portion 156 formed, for example, of EVA. An outer portion 154 of the wall 152 made, for example, of polyurethane surrounds the inner portion 156. With this arrangement, the diffusion rate of iodine into the inner portion 156 of the wall 152 is greater than the diffusion rate through the outer portion 154 to the outer surface 162. Thus an amount of iodine reaching the outer surface 162 is limited as desired, and the charge of anti-infective agent present in the lumen 160 will last for a longer period of time. Those skilled in the art will understand that the properties (materials, thickness, durometers, etc.) of the inner and outer portions 156, 154, respectively, may be adjusted to attain desired diffusion rates for various agents.

Figure 5:
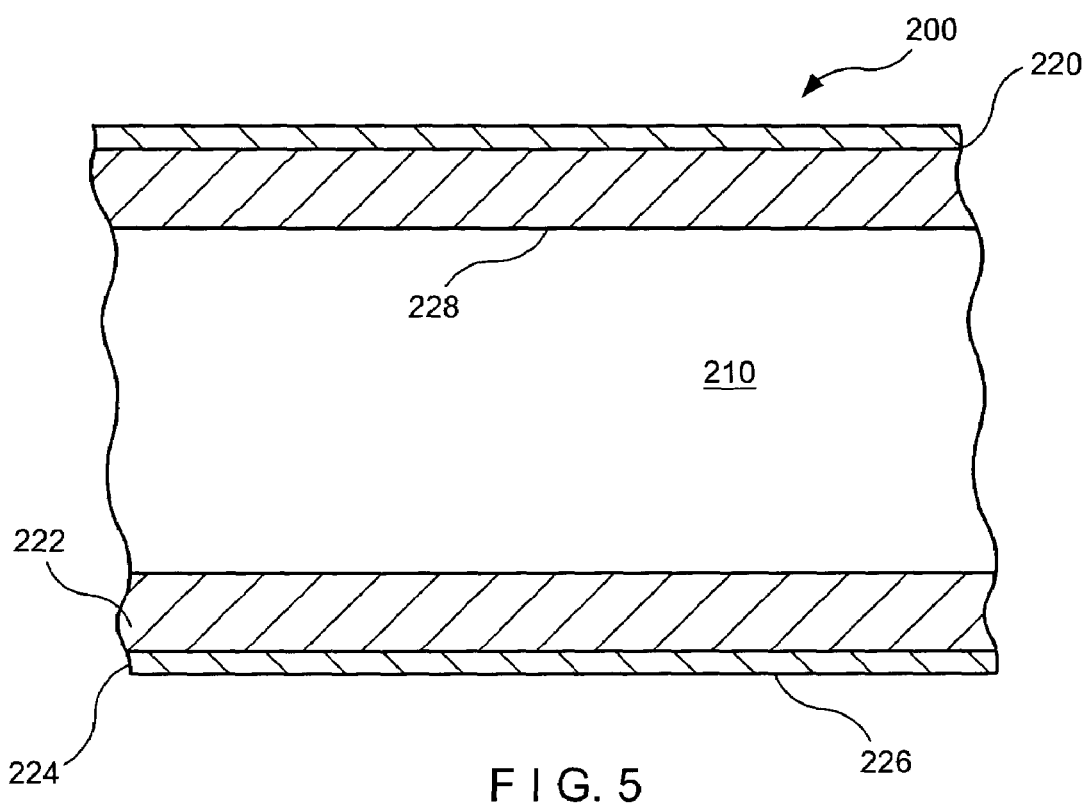
FIG. 5 is a diagram of a catheter cross section with an outer sheath according to a third embodiment of the present invention.

FIG. 5 shows a schematic diagram of another embodiment of a controlled diffusion catheter according to the present invention. In this exemplary embodiment, a catheter 200 includes an outer wall 220 formed of an inner portion 222, which, as described above, have a first diffusion rate with respect to anti-infective agents to be supplied to the catheter 200 contained within lumen 210. A coating 224 is formed around an outer surface of the inner portion 222. The coating 224 is formed of a material having a diffusion rate of the anti-infective agents which is slower than that of the inner portion 222. For example, the inner portion 222 may be formed of polyurethane while the coating 224 may be selected from a group of biostable polymers including polymers of polyolefins (polyethylene, PVC, PVF, PTFE), polyurethanes (silicones, fluorsilicones, polycarbonate-polyurethane-silicones), cellulosics such as cellulose acetate, polyesters, polyamides (hydroxy amide ethers), polyacrylates, liquid crystal polymers, polystyrene, polycarbonate, polyvinyl alcohols and polyethylene-vinyl alcohol while the inner portion 222.

Figure 6:
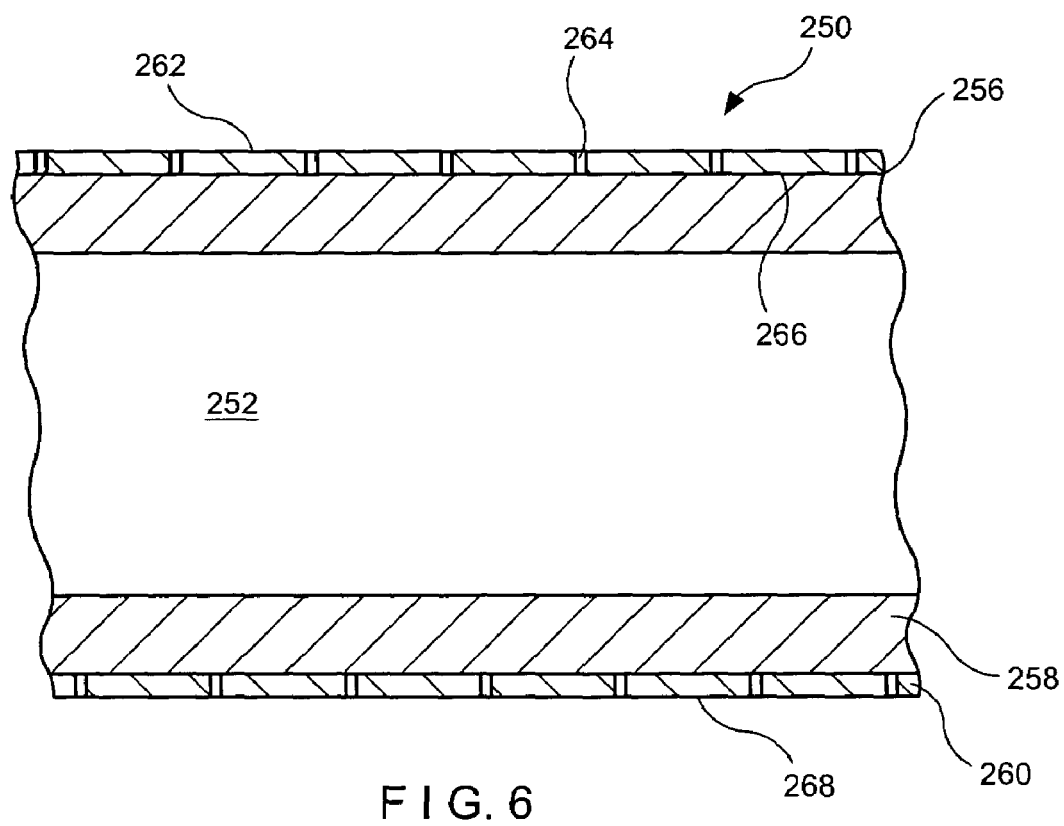
FIG. 6 is a diagram of a catheter cross section with a different sheath according to a fourth embodiment of the present invention.

In a further exemplary embodiment, an impermeable coating may be applied to the surface of an outer wall of the catheter according to the present invention. A secondary process may be used to form pores or channels of a predetermined size and distribution in the impermeable coating, to permit a predetermined level of diffusion of the anti-infective agent therethrough. As shown in FIG. 6, a catheter 250 includes an outer wall 256 disposed around a lumen 252. As described above, a therapeutic compound such as an anti-infective agent may be supplied to a lumen 252. As described above, an inner portion 258 of the outer wall 256 which contacts the contents of the lumen 252, preferably has diffusion properties with respect to the contents of the lumen 252 which allow a therapeutic agent to be quickly absorbed thereinto. An impermeable coating 260 is formed around an outer surface of the inner portion 258, forming a cladding around the entire surface of the catheter 250.

According to this exemplary embodiment of the invention, the impermeable coating 260 is processed so that a plurality of pores 264 are formed therein, extending from the inner surface 266 to an outer surface 268 of the coating 260. The coating 260 formed of a material that is substantially impermeable by the therapeutic agent to be supplied to the lumen 252. Thus, the only way that the agent can reach the outer surface 268 is via the pores 264. By properly selecting the number, size and configuration of the pores 264, a desired diffusion rate through the coating 260 may be obtained. Furthermore, this diffusion rate may be varied along the length or around the circumference of the catheter 250 by altering the distribution or size of the pores 264 if an amount of therapeutic agent required at a given location varies. As a result, the therapeutic agent in the lumen 252 is quickly absorbed into the inner surface of the catheter 250 and reaches the surface 264 at a desired rate to provide a controlled amount of protection against infective growth without unduly depleting the supply of therapeutic agents in the lumen 252.

As would be understood by those of skill in the art, the pores 264 may be formed by any of a mechanical machining process, an etching process, laser drilling or through the use of known photolithographic methods. It will be understood by those of skill in the art that the coating 260 may be formed of any material that is impermeable to the therapeutic agent which is to be supplied to the lumen 252, and that can be processed to form the desired pores 264. For example, the coating 260 may be formed, for example, from an impermeable polymer such as PET.

The present invention has been described with reference to specific exemplary embodiments. Those skilled in the art will understand that changes may be made in details, particularly in matters of shape, size, material and arrangement of parts. For example, although the present description referred to an exemplary dialysis catheter containing iodine or another anti-infective agent, the invention is not so limited. In addition, although the invention has been described in regard to single lumen catheters, in the case of a dialysis catheter, there would generally be included two lumens—a first for withdrawing blood from the patient and a second for returning treated blood to the patient. Those skilled in the art will understand that the same construction of a catheter as described above including an outer wall formed of an inner portion having a first rate of agent diffusion and an outer portion with a second rate of agent diffusion may be applied to multi-lumen catheters including any number of lumens. That is, so long as the inner portion of the catheter wall surrounds the one or more lumens to which the agent is to be supplied, a first rate at which the agent is to be absorbed into the inner portion will be determined by the properties of the inner portion while the properties of the outer portion of the catheter wall will determine the rate at which agent absorbed into the inner portion is supplied to an outer surface of the catheter. Accordingly, by selecting the materials and properties of the inner and outer portions of the catheter wall, the rate of absorption of agents into the inner catheter wall and the rate of diffusion of the agents to the outer surface of the catheter may be varied to maximize efficiency in the application of these agents.

Various other modifications and changes may be made to the embodiments described herein without departing from the broadest scope of the invention as set forth in the claims that follow. The specifications and drawings are, therefore, to be regarded in an illustrative rather than a restrictive sense.

What is claimed is:

1. A catheter extending from a distal end which, when in an operative position is inserted within a body of a patient, to a proximal end, the catheter comprising:
a charge holding cavity to which a therapeutic compound is to be supplied; and
a wall including inner and outer portions, an inner surface of the inner portion surrounding the charge holding cavity with the outer portion surrounding at least a portion of an outer surface of the inner portion, wherein the inner portion is formed so that a first diffusion rate of the therapeutic compound therethrough is different from a second diffusion rate through the outer portion, wherein a material of which the outer portion is formed is harder than a first material of which the inner portion is formed.

2. The catheter according to claim 1, wherein the second diffusion rate is lower than the first diffusion rate.

3. The catheter according to claim 1, wherein the inner and outer portions are coextruded.

4. The catheter according to claim 1, wherein the outer portion is less absorptive of the therapeutic compound than the inner portion.

5. The catheter according to claim 1, wherein the therapeutic compound is an anti-infective agent.

6. The catheter according to claim 5, wherein the anti-infective agent includes iodine.

7. The catheter according to claim 1, further comprising a rod impregnated with the therapeutic compound, the rod being insertable into the charge holding cavity.

8. The catheter according to claim 1, wherein the charge holding cavity comprises a lumen of the catheter.

9. The catheter according to claim 1, wherein the inner portion is formed of a polymer and the outer portion is formed of a polymer including one of barium sulfate, titanium oxide and bismuth sub-carbonate.

10. The catheter according to claim 1, wherein the inner and outer portions are formed of different materials.

11. The catheter according to claim 1, wherein the outer portion contains polyurethane and the inner portion contains EVA.

12. The catheter according to claim 1, wherein the outer portion is formed as a coating surrounding at least a portion of an outer surface of the inner portion.

13. The catheter according to claim 12, wherein the coating is formed of one of polymers of polyolefins, polyurethanes, cellulosics, polyesters, polyamides, polyhydroxy amide ethers, polyacrylates, liquid crystal polymers, polystyrene, polycarbonate, polyvinyl alcohols and polyethylene-vinyl alcohol.

14. The catheter according to claim 1, wherein the outer portion is formed as a coating of a material which is substantially impermeable with respect to the therapeutic compound, wherein a plurality of pores extend through the outer portion to permit the therapeutic compound to pass therethrough from the inner portion to an outer surface of the outer portion.

15. The catheter according to claim 14, wherein the pores are formed by one of machining, an etching process and photolithography.

16. The catheter according to claim 1, wherein the inner and outer portions are formed of different materials.

17. The catheter according to claim 1, wherein the outer portion contains polyurethane and the inner portion contains EVA.

18. The catheter according to claim 1, wherein the outer portion is formed as a coating surrounding at least a portion of an outer surface of the inner portion.

19. The catheter according to claim 18, wherein the coating is formed of one of polymers of polyolefins, polyurethanes, cellulosics, polyesters, polyamides, polyhydroxy amide ethers, polyacrylates, liquid crystal polymers, polystyrene, polycarbonate, polyvinyl alcohols and polyethylene-vinyl alcohol.

20. The catheter according to claim 1, wherein the outer portion is formed as a coating of a material which is substantially impermeable with respect to the therapeutic compound, wherein a plurality of pores extend through the outer portion to permit the therapeutic compound to pass therethrough from the inner portion to an outer surface of the outer portion.

21. The catheter according to claim 20, wherein the pores are formed by one of machining, an etching process and photolithography.

* * * * *